United States Patent [19]

Lodder

[11] Patent Number: 5,553,610
[45] Date of Patent: *Sep. 10, 1996

[54] APPARATUS AND METHOD FOR NONINVASIVE CHEMICAL ANALYSIS

[75] Inventor: Robert A. Lodder, Nicholasville, Ky.

[73] Assignee: University of Kentucky Research Foundation, Lexington, Ky.

[*] Notice: The term of this patent shall not extend beyond the expiration date of Pat. No. 5,402,782.

[21] Appl. No.: 385,244

[22] Filed: Feb. 7, 1995

Related U.S. Application Data

[63] Continuation of Ser. No. 26,705, Mar. 5, 1993, Pat. No. 5,402,782.

[51] Int. Cl.$^6$ .................................................. A61B 5/00
[52] U.S. Cl. ............... 128/633; 128/653.1; 128/660.01; 128/664; 250/341.1; 436/71; 436/171
[58] Field of Search ............................. 128/653.1, 660.01, 128/664, 633; 73/61.48, 61.49, 602, 645, 587; 424/9; 436/71, 150, 171; 250/339.01, 339.11, 340, 341.1, 341.8

[56] References Cited

U.S. PATENT DOCUMENTS

| | | |
|---|---|---|
| 4,765,179 | 8/1988 | Fuller et al. |
| 4,767,719 | 8/1988 | Finlan |
| 4,801,552 | 1/1989 | Hoff |
| 4,935,875 | 6/1990 | Shah et al. |
| 5,064,638 | 11/1991 | Moore et al. |
| 5,402,782 | 4/1995 | Lodder .................................. 128/653.1 |

OTHER PUBLICATIONS

R. A. Lodder; G. M. Hieftje; W. Moorehead; S. P. Robertson; P. Rand. Assessment of the feasibility of determination of cholesterol and other blood constituents by near–infrared reflectance analysis, *Talanta*, 36, 193–198, 1989.

Cassis, L. A.; Lodder, R. A. Near–IR imaging of atheromas in living arterial tissue. Submitted to *Anal. Chem.*, 1992.

Lai, E. P. C.; Chan, B. L.; Chen, S. Ultrasonic resonance spectroscopic analysis of microliters of liquids. *Appl. Spectrosc.* 1988, 42, 526–529.

Keltner, J. R.; Roos, M. S.; Brakeman, P. R.; Budinger, T. F. Magnetohydrodynamics of blood flow. *Magn. Reson. Med.* 1990, 16(1) 139–149.

Mills, Timothy P.; Lodder, Robert A. Acoustic–Resonance Spectrometry with Multivariate Analysis for the Identification of Wood Species.

The Pittsburgh Conference on Analytical Chemistry and Applied Spectroscopy. New Orleans, LA Mar. 1992.

Gebhart, Brian D.; Lodder, Robert A. A Novel Acoustic–Resonance Spectrometer Pittsburg Conference, Atlanta, GA Mar. 1989.

*Primary Examiner*—Ruth S. Smith
*Attorney, Agent, or Firm*—King and Schickli

[57] ABSTRACT

A method and apparatus are provided for magnetohydrodynamic acoustic-resonance, near-IR spectroscopy. The method includes a step of applying to a subject under study a magnetic field having a strength between 2,00–10,000 gauss, near-IR radiation having a wavelength between 800–3,000 nm and an acoustic wave having a frequency between 10 khz –1 Mhz. The method also includes the steps of inducing vibration of ions in the magnetic field and detecting an electric wave generated magnetohydrodynamically by the acoustic wave induced vibration of the ions. Next is the collecting of the electrical, acoustical and near-IR spectra and the analyzing of the collected spectra. The spectra is analyzed in a hyphenated, multidimensional fashion.

6 Claims, 2 Drawing Sheets

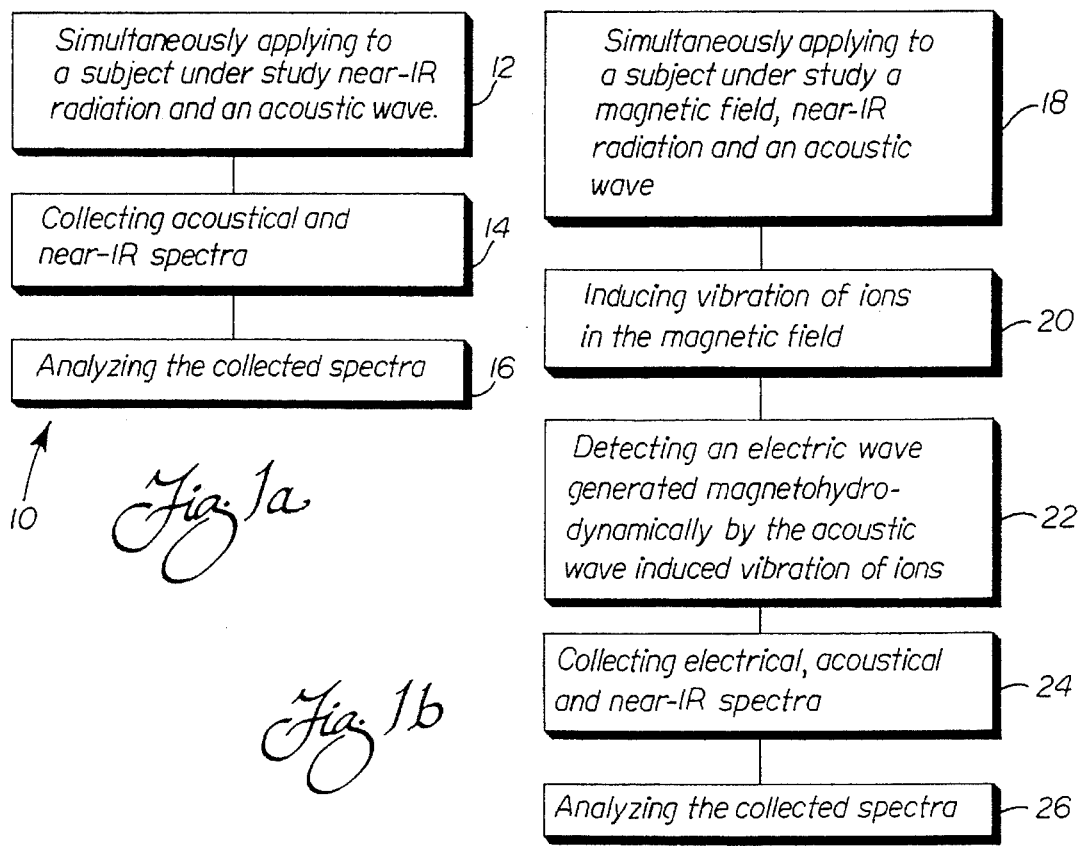
Fig. 1a
Fig. 1b
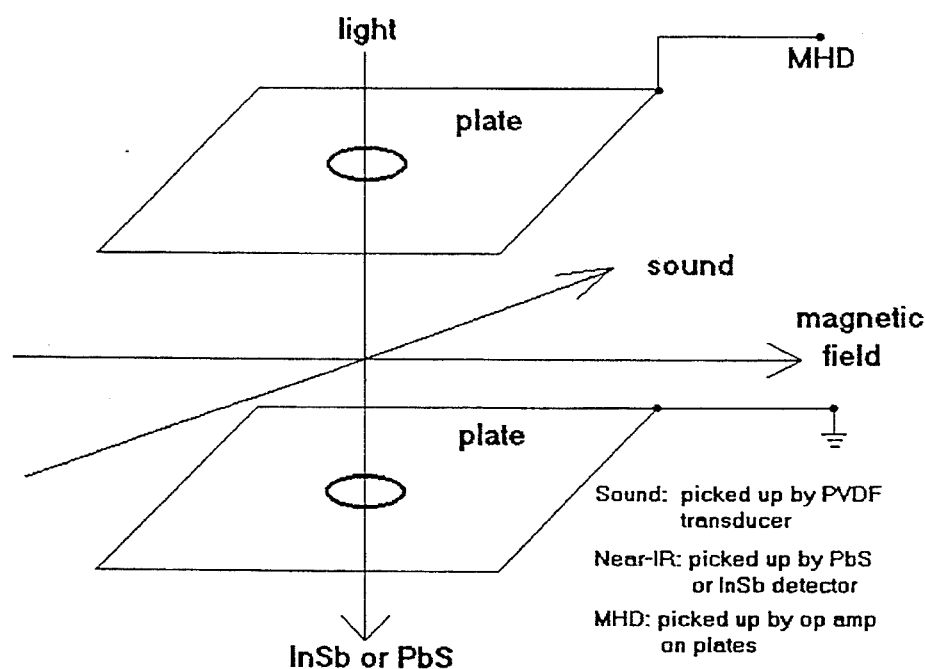
Fig. 2

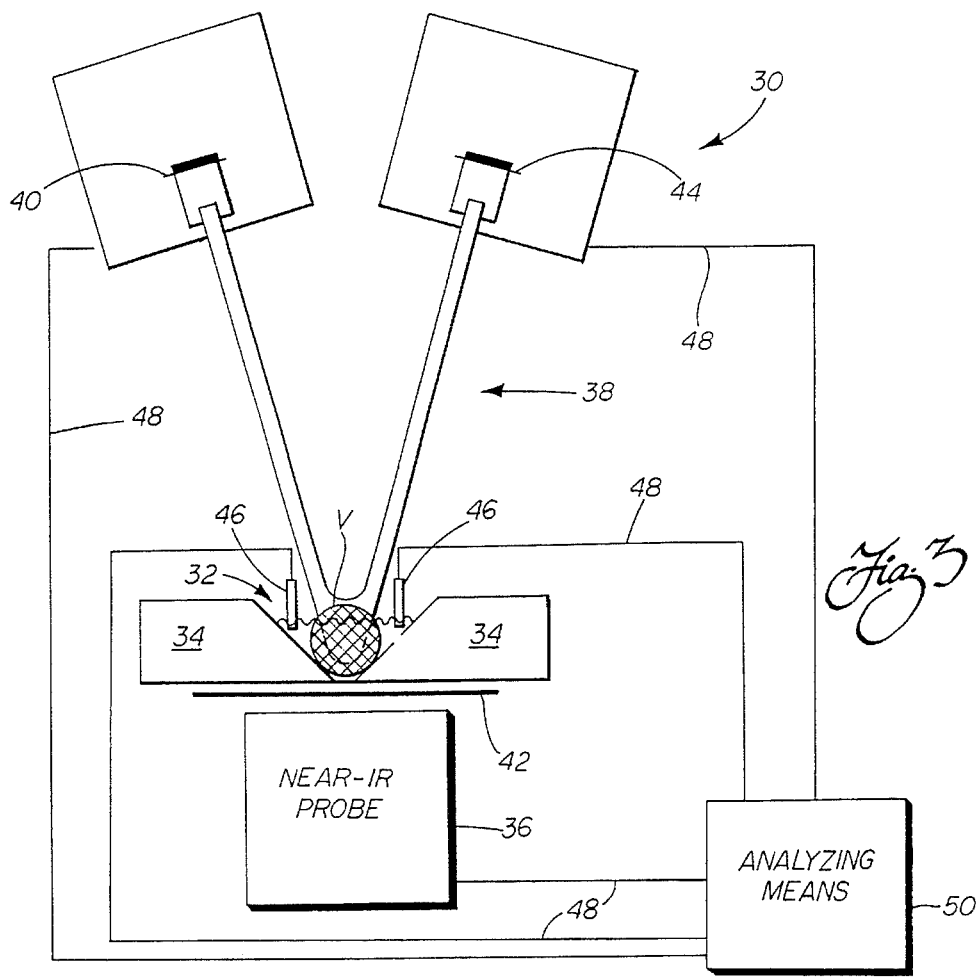
Fig. 3
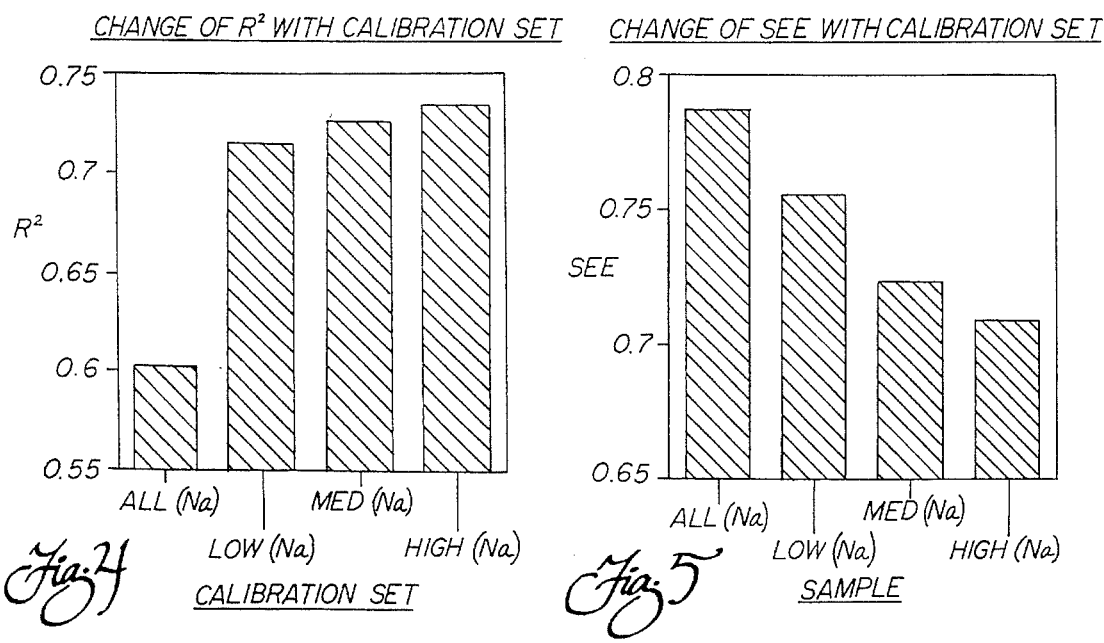
Fig. 4
Fig. 5

APPARATUS AND METHOD FOR NONINVASIVE CHEMICAL ANALYSIS

This is a continuation of application Ser. No. 08/026,705, filed Mar. 5, 1993, U.S. Pat. No. 5,402,782.

TECHNICAL FIELD

The present invention relates generally to a method and apparatus for the chemical analysis of a selected specimen or subject through the simultaneous utilization of acoustic-resonance waves and near-IR radiation alone or in conjunction with a magnetic field.

BACKGROUND OF THE INVENTION

Various analytic and diagnostic approaches have been devised for noninvasive chemical analysis. Such approaches include, for example, near-IR spectrometry and acoustic-resonance spectrometry.

More specifically, as disclosed in co-pending U.S. patent application Ser. No. 945,202, filed Sep. 15, 1992 and entitled APPARATUS AND METHOD FOR ANALYZING TISSUE, (the disclosure of which is fully incorporated herein by reference), near-IR spectrometry may be utilized, for example, to determine the presence and relative concentrations of cholesterol and lipoproteins in a human blood matrix. The article "Ultrasonic Resonance Spectroscopic Analysis of Microliters of Liquids", *Applied Spectroscopy*, Volume 42, No. 3, 1988, pp. 526–529, describes a method of utilizing ultrasonic resonance techniques for the identification of microliters of liquids. This ultrasonic technology is also already used to sense the types and amounts of gasses in an air sample by detecting resonant frequency shifts.

Up to the date of the present invention, however, near-IR spectrometry and acoustic-resonance spectrometry have only been utilized separately and not in combination. Advantageously, the present inventor has now found that the two techniques may be utilized together in a "hyphenated" fashion to achieve a surprising, synergistic and more powerful result. Specifically, ultrasound and near-IR light may be made to interact to provide additional selectivity for targeted analytes in a sample. Further, the present inventor has found that the addition of powerful magnets adds a third dimension to the analysis by enabling detection of ultrasonically induced electrical currents in the sample. Thus, the concentration of electrolytes in a specimen or subject undergoing analysis may be determined accurately and noninvasively. This information may then be utilized to essentially eliminate near-IR spectral interference from water thereby enhancing the sensitivity and performance of this novel analytical technique.

SUMMARY OF THE INVENTION

Accordingly, it is a primary object of the present invention to provide a method and apparatus for combining near-IR spectrometry and acoustic-resonance spectrometry to provide enhanced analysis capabilities that may, advantageously, be utilized in vitro or in vivo. Such capabilities allow noninvasive and nondestructive determination of the concentration of substantially any biological molecule or ion in an aqueous environment. This information may then be utilized in the early diagnosis of certain medical risks and disorders and thereby advantageously allow early administration of effective treatment to a patient.

Still another object of the present invention is to provide a method and apparatus for magnetohydrodynamic/acoustic-resonance/near-IR spectrometry (MARNIR) wherein the specimen or subject is simultaneously subjected to the application of near-IR radiation, a tunable acoustic wave and a magnetic field. Advantageously, spectral interference from water is mathematically eliminated by noninvasively determining the total concentration of electrolytes in the specimen or subject. Specifically, the ions are nondestructively vibrated with ultrasound in a magnetic field thereby inducing an electric current with an amplitude proportional to the amount or concentration of electrolytes present.

Still another, more specific, object of the present invention is to provide a new diagnostic method for quantification of cholesterol and lipoproteins in a noninvasive and nondestructive manner either in a blood specimen in vitro or in a mammal such as a human in vivo.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, a method and apparatus are provided for acoustic-resonance, near-IR spectroscopy. In accordance with this analytic and diagnostic technique, enhanced, nondestructive/non-invasive identification of nonelectrolytes (eg. nonelectrical conducting materials) in serum samples and the body is possible. More specifically, the method for acoustic-resonance, near-IR spectroscopy comprises the steps of simultaneously applying to a subject under study near-IR radiation and an acoustic wave, collecting acoustical and near-IR spectra and analyzing the collected spectra.

Still more specifically, the near-IR radiation utilized has a wavelength between 800–3000 nm. Preferably, this entire wavelength spectrum is applied simultaneously and in parallel with equal weighting being given to each wavelength so as to ensure that any variations in absorbance at any wave-length for the subject undergoing study is observed. As all tissues and chemical analytes absorb light across all these wavelengths, with tissues and analytes absorbing only a little more at some wavelengths than others, this broad band parallel approach is necessary to ensure that no unusual tissue or analyte is missed during study. Accordingly, the analysis is more accurate and complete. Further, as the analysis is performed in parallel, the complete study may still be completed in a sufficiently short time span to allow clinical utilization of this technology.

The tunable acoustic wave that is applied to the subject under study preferably has a frequency of between 10 khz–1 Mhz. Advantageously, by tuning the acoustic wave in accordance with the known characteristics of the analyte for which an assay or analysis is being completed, it is possible to improve identification and quantification for that analyte. For example, similar apolipoproteins, such as apoA-I and apoA-II, may be more readily distinguished in solution. Specifically, the acoustic wave form modulates the confirmation and hence the near-IR spectra of these compounds through hydrogen bonding. In addition, the acoustic wave may be tuned to help to set the near-IR spectral baseline by establishing the bulk density of tissue samples in vivo.

In accordance with yet another aspect of the method, the acoustical and near-IR spectra that are collected are analyzed in a hyphenated, multi-dimensional fashion.

In accordance with yet another aspect of the present invention, a magnetic field is applied to the subject under study simultaneously with the near-IR radiation and acoustic wave in order to provide magnetohydrodynamic, acoustic-resonance, near-IR spectroscopy or MARNIR. Specifically, the magnetic field, near-IR radiation and acoustic wave are all applied to the subject in independent planes that are orthogonal to one another. The addition of the powerful magnetic field adds another dimension to the analytical capability of the present invention by enabling detection of ultrasonically induced electrical currents in the sample. Accordingly, it is possible to overcome a notable limitation of simple near-IR spectrometry that is imposed by spectral interference from water.

More specifically, the near-IR spectral bands of water change in response to temperature, pH and the concentration of other ions in the water. These all effect the extent of hydrogen bonding. The spectra of analytes like cholesterol are easily obscured by changes in the water spectrum which is the most intense spectrum observed in the near-IR. As the water interference can be removed mathematically from near-IR spectra if the total electrolytes can be determined, the present method is particularly advantageous as the total electrolytes may be determined noninvasively and nondestructively by vibrating the ions with ultrasound and inducing an electrical current with an amplitude proportional to the amount of electrolytes present. As a result, enhanced sensitivity and performance are provided efficiently and noninvasively to achieve more reliable and accurate quantitative analysis.

In the most preferred form of the invention, the magnetic field has a strength between 2000–10000 gauss. Such a field strength allows the ions vibrated by the acoustic wave to produce a sufficiently strong electrical current to allow reliable detection and accurate determination of ion concentration.

In accordance with yet another aspect of the present invention, an apparatus is provided for performing acoustic-resonance, near-IR spectroscopy. The apparatus includes means for irradiating the subject with near-IR radiation and means for simultaneously producing a tunable acoustic wave that is transmitted into and through the subject. Additionally, the apparatus includes means for collecting acoustical and near-IR spectra that result. Means, such as a supercomputer, for analyzing the spectral data in accordance with the algorithm described above is also provided.

Still further, an apparatus for performing MARNIR of a subject under study also includes means for producing a magnetic field and means for detecting electrical waves generated magnetohydrodynamically by the acoustic wave induced vibration of ions in the magnetic field. In this way, the ion concentration of the subject/specimen may be noninvasively deduced. Further, means are provided for simultaneously collecting the electrical spectra that result and this spectra is simultaneously analyzed along with the acoustical and near-IR spectra for accurate and complete analysis.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWING

The accompanying drawing incorporated in and forming a part of the specification, illustrates several aspects of the present invention, and together with the description serves to explain the principles of the invention. In the drawing:

FIG. 1a and 1b are schematic block diagrams illustrating the methods of the present invention;

FIG. 2 is schematical representation showing the orthogonal application of the acoustic resonance wave, near-IR radiation and magnetic field to a subject;

FIG. 3 is a schematical representation of the apparatus of the present invention; and FIGS. 4 and 5 are histograms showing, respectively, the correlation and standard error of estimate for cholesterol in aqueous solutions containing sodium ions.

Reference will now be made in detail to the present preferred embodiment of the invention, an example of which is illustrated in the accompanying drawing.

DETAILED DESCRIPTION OF THE INVENTION

Reference is now made to the schematic block diagram shown in FIG. 1a describing the method of the present invention for simultaneous acoustic-resonance, near-IR spectroscopy. That method 10 includes the initial step 12 of simultaneously applying to a subject under study both near-IR radiation and an acoustic wave. "Subject under study" is being broadly utilized to refer to a collected biological specimen held in a vial or container that is undergoing in vitro analysis or a mammal such as a human that is undergoing in vivo analysis.

Preferably, the near-IR radiation that is applied to the subject has a wavelength of between 800 and 3,000 nm. Still more preferably, light across the full wavelength spectrum of 1,500–2,100 nm and, more preferably, 800–3,000 nm is applied simultaneously and in parallel. This is done because major spectral changes indicating the presence of a selected analyte, such as low-density lipoprotein (LDL) may be observed in this range. In order to determine the presence of these low-density lipoproteins with analytical precision it is desired to utilize light across the full spectrum indicated. This is because tissues and analytes absorb light at all wavelengths across this range and different tissues and analytes absorb only a little more at some wavelengths than others. As the chemical make-up of the subject under study is unknown, the particular wavelength(s) where these differences occur are also unknown in advance. It is, therefore, necessary to analyze the entire range with each wavelength being given equal weight in the analysis.

Further, this must be done simultaneously and in parallel to ensure a speed of imaging necessary to make this method acceptable for clinical applications. Only in this way is it possible to avoid missing the presence of unusual tissues or analytes of interest to the clinician completing the study.

The acoustic wave applied to the subject preferably has a frequency between 10 khz–1 Mhz. Still more preferably, the frequency is tunable so that the technician may perform a series of steps to enhance the performance and sensitivity of the method and achieve sharply enhanced analytical results. Specifically, the acoustic wave spectrum may, for example, be patterned to help set the near-IR spectral baseline by establishing the bulk density of the tissue samples in vivo. This may best be done by, for example, using the ARS spectrum to determine acoustic velocity of the tissue by examining the magnitude of the phase shifts observed in the sample signal at several ARS spectral peaks.

The acoustic wave spectrum may also be tuned and thereby utilized to improve identification and quantification of similar analytes such as apolipoproteins (such as apoA-I and apoA-II) in solution. More specifically, their conformations and hence their near-IR spectra are modulated through hydrogen bonding. This may be done by using a standing wave, which may be a compression or rarefaction, to make a large molecule adopt a certain conformation.

Performed in combination with the application of the near-IR radiation and acoustic wave is the step 14 of collecting acoustical and near-IR spectra from the subject. These spectra are collected simultaneously and in parallel. Specifically, equal weight is given to each wavelength of radiation over the applied 800–3,000 nm near-IR band spectrum at the frequency of the acoustic wave being applied and collected.

The collected acoustical and near-IR spectra are then analyzed in a hyphenated, multidimensional fashion (step 16). More specifically, the spectral data is analyzed in accordance with the copyrighted 3N-BEST Algorithm software as authored by Robert A. Lodder. Specifically, the collected near-IR and acoustic wave spectra are digitized for analysis on a processor such as an IBM 3090-600J super computer as available at the University of Kentucky.

In accordance with yet another aspect of the present invention and as represented in the schematic block diagram shown in FIG. 1b, a magnetic field may be simultaneously applied (step 18) to the subject under study with the near-IR radiation and tunable acoustic wave. Preferably, the magnetic field, near-IR radiation and acoustic wave are applied to the subject in planes orthogonal to one another such as shown in FIG. 2. This spatial relationship is preferred because the acoustic wave should be perpendicular to the magnetic field to maximize current flow, and the near-IR light should be perpendicular to the acoustic wave in order to selectively sample conformations in compressions or rarefactions in a standing wave. For purposes of illustration, the orthogonal sampling arrangement being described is shown relative to a rectangular sample cell or vial in FIG. 2.

More specifically, the applied magnetic field preferably has a strength of between 2,000–10,000 gauss while the near-IR radiation has a wavelength between 800–3,000 nm and the acoustic wave has a frequency between 10 khz–1 Mhz. The addition of the powerful magnetic field furnishes a third dimension to the analysis thereby enabling detection of ultrasonically induced electrical currents in the subject. Advantageously, this ability makes it possible to overcome a notable limitation of simple near-IR spectrometry that is imposed by the spectral interference from water.

Near-IR spectral bands of water change in response to changes in temperature, pH and the concentration of other ions in the water. This is because these all effect the extent of hydrogen bonding. As the most intense spectrum observed in the near-IR is the water spectrum, the spectra of analytes, like cholesterol, are easily obscured by changes in the water spectrum. This problem of obscured results may be avoided by mathematically removing the water interference from near-IR spectra where the total electrolytes can be determined. Advantageously, the present method allows the total concentration of electrolytes to be determined noninvasively and nondestructively by vibrating the ions with ultrasound in the magnetic field, thereby inducing an electrical current with an amplitude proportional to the amount/concentration of electrolytes.

Specifically, the acoustic wave may be tuned to induce ion motion in the magnetic field (step 20). The moving ions, such as sodium ions, create an electrical current that is detected by electrodes (step 22). By measuring the current continuously in a computerized pattern algorithm the ion concentration is revealed thereby permitting accurate analysis of, for example, cholesterol and other analytes through the substantial elimination of near-IR spectral interference from water.

In combination with the simultaneous application of the magnetic field, near-IR radiation and tunable acoustic wave is the simultaneous collecting of electrical, acoustical and near-IR spectra (step 24). This is followed by the analyzing of the collected spectra in the hyphenated, multidimensional fashion (step 26). Specifically, the 3N-BEST Algorithm software is utilized.

The basic principle behind this software is to represent the complete near-IR, acoustic-resonance, and magnetohydrodynamic spectra of a sample as a single direction vector in a thrice-augmented hyperspace with a length that is an asymmetric probability. The output of the 3N-BEST Algorithm software can then be analyzed directly by discriminant analysis or by traditional methods like partial least squares or principal component regression, or can be analyzed by more sophisticated full-spectra techniques like the BENDS algorithm.

Specifically, the acoustic spectrometers collect either 128, 452 or 16,384 data points per spectrum. Thus, if the middle value is chosen as the default, a single scan under the present method can be represented as a point in a 1605 dimensional space (701+452+452). If the data are analyzed in a more accurate hyphenated configuration, one obtains a 316,852 dimensional space (701×452×452). In this latter case the spectra cannot be represented as a single line with peaks and valleys. Instead, each individual spectrum has to be drawn as a three-dimensional figure, making the display considerably more difficult.

The algorithm, however, does not require a display of individual spectra in order to produce an analytical result; that is, the identity and quantity of each constituent. Accordingly, when the present method is utilized to quantify cholesterol and lipoproteins simultaneously in serum samples and/or in vivo, sufficiently accurate analysis is possible to advantageously allow, for example, accurate predictions of the risks of stroke in a patient. Additionally, the present method readily allows the effectiveness of a treatment regimen to be closely monitored and adjustments made as necessary in order to provide more effective treatment. Further, as the overall method minimizes sample handling as well as time of analysis, measurements of in vitro specimens/samples, in particular, are more accurate. This is because of a resulting reduction in degradation of the analyte (e.g. lipoprotein) being assayed.

In accordance with still another aspect of the present invention, an apparatus for conducting magnetohyrodynamic, acoustic-resonance, near-IR spectroscopy is schematically shown and will now be described with reference to FIG. 3. The apparatus 30 being described is designed for in vitro analysis of, for example, a biological specimen contained in a vial V. It should be appreciated, however, that a similar arrangement may be utilized to analyze a subject such as a mammal in vivo.

As shown in FIG. 3, the vial V is positioned so as to rest at the bottom of a V-shaped slot 32 formed between a pair of opposed, samarium cobalt magnets 34. Such magnets have a field strength of between 2,000–10,000 gauss. Magnets of the type utilized are available, for example, from Edmond Scientific, catalog No. A30,730 ring magnets, 8000 gauss.

As further shown in FIG. 3, a near-IR probe 36 is positioned beneath the sample vial V. A near-IR probe 36 of the type that may be utilized includes a tungsten-halogen lamp with wavelength selection being accomplished utilizing a concave holographic diffraction grating in combination with a lead sulfide (Pbs) or indium antimonide (InSb) detector cooled with liquid nitrogen. Commercially available near-IR probes 36 may be obtained from a number of sources including, Bran+Luebbe, such as the Bran+Luebbe EDAPT 1. Preferably, the near-IR probe 36 is capable of producing a light spectrum having a wavelength of between 800–3,000 nm (at least 1,500–2,100 nm). Light over this full spectrum is preferably applied simultaneously and in parallel to the specimen in the vial V.

As further shown, the apparatus 30 also includes an acoustic wave generator/receiver generally designated by reference numeral 38. The acoustic wave generator/receiver 38 includes transmitting piezo films 40, 42 and receiving piezo film 44. Films that may be utilized for this purpose include polyvinylidene fluoride films such as available from Atochem Sensors, Inc. These films are capable of transmitting and receiving a tunable acoustic waveform having a frequency of between 10 khz and 1 Mhz.

After collecting and placing a biological specimen in the vial V, the vial is sealed and positioned in the V-shaped slot 32 between the magnets 34. A scan is then initiated. Accordingly, the specimen in the vial V is simultaneously subjected to a magnetic field of 8,000 gauss, near-IR radiation across a full spectrum of, preferably, 800–3,000 nm and a tunable acoustic wave having a frequency of between 10 khz and 1 Mhz. The frequency of the acoustic wave that is chosen is usually determined by the ultrasonic characteristics of the analyte for which assaying or analysis is being completed. When assaying a specimen for overall chemical make-up, a selected series of frequencies or a sweep through the full frequency range may be performed.

Advantageously, the acoustic wave that is transmitted through the specimen in the vial V causes ions in the aqueous medium to vibrate. These ions, such as sodium ions, produce an electric current in the magnetic field as a result of their vibration. The resulting electrical spectra is collected by a pair of opposed magnetohydrodynamic electrodes (MHD electrodes) 46 placed beside the specimen vial V at 90° to the samarium cobalt magnets 34. Such electrodes 46 may be constructed from common electronics parts available from a number of sources. Gold or platinum wire is preferred in the construction.

The resulting electrical spectra is collected simultaneously along with the near-IR and acoustic wave spectra. Specifically as shown, the spectral data is collected and delivered along signal lines 48 for analysis utilizing a processor such as a super computer 50. The 3N-BEST software/algorithm analysis is then completed as required to provide the desired quantitative assay.

In early experiments, the apparatus 30 described above has been utilized to obtain experimental data from twenty-seven calibration samples containing various amounts of sodium chloride (0, 0.8752 and 1.75 mg/ml) and cholesterol (0, 1, 2, 3, 4 mg/ml). First, near-IR scans (e.g. near-IR spectroscopy alone) of five samples with the same range of cholesterol concentrations from each of the three sodium ion concentration groups were analyzed by complete linkage cluster analysis. The results showed that the observed near-IR spectrum of cholesterol depends on the sodium concentration. Thus, the interference problem caused by ion concentration shifting of the near-IR water spectrum was demonstrated.

In subsequent tests utilizing full MARNIR capabilities, the mean magnetohydrodynamic signals observed at the op amp for the different levels of $Na^+$ in solution were 0.8 volts for 0 mg/ml of $Na^+$, 0.4 volts for 0.8752 mg/ml of $Na^+$ and 0.6 volts for 1.75 mg/ml of $Na^+$. The 0.8 volt value for the 0 mg/ml $Na^+$ concentration group actually results from what is known as "antenna effect." Specifically, the no sodium, deionized water utilized acted as an insulator and caused the MHD electrodes to function as antennas, picking up radiated radio frequency energy from the signal generator which was found to not be fully shielded. Otherwise, the detected MHD voltage was found to be directly proportional to sodium concentration thereby allowing the $Na^+$ concentration of a specimen to be accurately determined.

FIGS. 4 and 5 show how knowledge of the $Na^+$ concentration provided by acoustics and magnetohydrodynamics as applied in this invention improves the ability to noninvasively determine cholesterol concentrations. The first bar in each histogram shows the correlation ($R^2$) and standard error of estimate (SEE), respectively for cholesterol if $Na^+$ levels are unknown. In the second, third and fourth bars, the correlation and SEE are given for each group of samples with known $Na^+$ concentration determined by the detected magnetohydrodynamic signal. In each case, knowledge of $Na^+$ concentration improves that determination of cholesterol. Because the test apparatus of the present invention that was utilized in these early studies was only a prototype with limited sensitivity, the best signals and lowest errors in $Na^+$ concentration occur when analyzing the high $Na^+$ concentration group (1.75 mg/ml). It should be appreciated, however, that such a concentration level is still lower than physiologic $Na^+$ levels and, accordingly, utility of this method and apparatus for biological analysis is established.

In summary, numerous benefits have been described which result from employing the concepts of the present invention. Specifically, far more efficient and precise quantitative analysis capabilities are provided utilizing the present method and apparatus. Specifically, the presence of analytes may be determined in an accurate and efficient manner as the near-IR spectral interference from water is substantially eliminated in a nondestructive manner. Advantageously, the quick and efficient noninvasive and nondestructive approach of the present invention functions to provide a diagnostic technique of considerable importance such as may be utilized to predict the risks of stroke, confirm the existence of certain maladies and even monitor the effectiveness of treatment procedures.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with breadth to which they are fairly, legally and equitably entitled.

I claim:

1. A method for acoustic-resonance, near-IR spectroscopy comprising the steps of:

simultaneously applying to a subject under study near-IR radiation and an acoustic wave;

collecting acoustical and near-IR spectra emitted from the subject under study as a result of the applied near-IR radiation and acoustic wave; and analyzing the collected spectra.

2. The method set forth in claim 1, wherein said near-IR radiation and acoustic wave are applied to the subject in planes perpendicular to one another.

3. The method set forth in claim 1, wherein said acoustical and near-IR spectra collected are analyzed in a hyphenated, multidimensional fashion.

4. The method set forth in claim 3, wherein said near-IR radiation is a wavelength between 800–3000 nm and said acoustic wave has a frequency between 10 khz–1 Mhz.

5. An apparatus for acoustic-resonance, near-IR spectroscopy; comprising:

means for radiating a subject under study with near-IR radiation;

means for simultaneously producing a tunable acoustic wave that is transmitted into the subject under study;

means for collecting acoustical and near-IR spectra emitted from the subject under study as a result of the applied near-IR radiation and the acoustic wave; and means for analyzing the collected spectra.

6. The apparatus set forth in claim 5, further including means for applying said acoustic-resonance wave and near-IR radiation to said subject under study in planes perpendicular to one another.

* * * * *